United States Patent [19]

Sauerbier et al.

[11] Patent Number: 4,959,215
[45] Date of Patent: Sep. 25, 1990

[54] IFOSFAMIDE-MESNA LYOPHILIZATE AND PROCESS FOR ITS PREPARATION

[75] Inventors: Dieter Sauerbier, Werther; Otto Isaac, Hanau; Wolfgang P. Brade, Wehrheim, all of Fed. Rep. of Germany

[73] Assignee: Asta Pharma AG, Frankfurt am Main, Fed. Rep. of Germany

[21] Appl. No.: 325,883

[22] Filed: Mar. 20, 1989

[30] Foreign Application Priority Data

Mar. 19, 1988 [DE] Fed. Rep. of Germany ....... 3809337

[51] Int. Cl.$^5$ ............................................... A61K 9/00
[52] U.S. Cl. ..................................... 424/422; 424/423
[58] Field of Search ............... 424/422, 423, 465, 405, 424/464; 514/709, 712, 79, 89, 90, 137, 922

[56] References Cited

U.S. PATENT DOCUMENTS

| | | | |
|---|---|---|---|
| 4,623,742 | 11/1986 | Scheffler et al. | 558/81 |
| 4,716,242 | 12/1987 | Engel et al. | 558/81 |
| 4,859,452 | 8/1989 | Ajani et al. | 514/922 |
| 4,871,528 | 10/1989 | Tognella et al. | 514/922 |

*Primary Examiner*—Thurman K. Page
*Attorney, Agent, or Firm*—Cushman, Darby & Cushman

[57] ABSTRACT

An ifosfamide-mesna lyophilizate consists substantially of ifosfamide, 0.1–1.0 parts by weight of mesna and 0.1 to 17 parts by weight of hexitol. The product is obtained by freeze drying an aqueous or aqueous-ethanolic solution of ifosfamide and mesna.

8 Claims, No Drawings

IFOSFAMIDE-MESNA LYOPHILIZATE AND PROCESS FOR ITS PREPARATION

The present invention relates to compositions containing ifosfamide and mesna.

BACKGROUND OF THE INVENTION

The chemical name of the active substance ifosfamide is 3-(2-chloroethyl)-2-(chloroethylamino)-tetrahydro-2H-1, 3,2-oxazaphosphorin-2-oxide

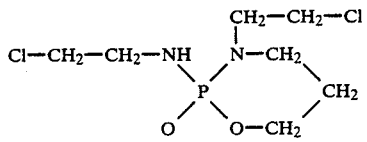

In common with cyclophosphamide, ifosfamide belongs to the chemical group of oxazaphosphorins and is used therapeutically for the treatment of tumor diseases.

The chemical name of the uroprotector mesna is sodium2-mercaptoethanesulphonate.

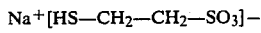

Mesna protects, for example, the urinary tract in the treatment of tumor diseases with ifosfamide, this uroprotective action of mesna being present in particular when it is administered simultaneously and synchronously together with ifosfamide.

Ifosfamide is a white crystalline powder having a melting point of 48° C. to 51° C. and pronounced hygroscopic properties. Ifosfamide begins to sinter below its melting point and must therefore be stored at temperatures that are as low as possible (room temperature and below). Contact with humidity is also to be avoided as much as possible.

Ifosfamide dissolves in water to the extent of about 10 percent by weight, but is only stable to a limited extent in aqueous solution (a maximum of 3 to 4 hours at 20° C. to 22° C. or 36 hours at 4° to 6° C.

Ifosfamide is only administered parenterally. The injection bottles contain 200 to 5000 m of ifosfamide in the form of a sterile crystallizate which is dissolved in water for injection purposes before administration so that a 4% concentration is not exceeded. This solution is suitable for intravenous injection. For intravenous short infusion the ifosfamide solution is dissolved in 500 ml of Ringer's solution or a similar infusion liquid. The duration of the infusion is ca. 30 minutes, possibly 1 to 2 hours. In the case of the 24-hour infusion, the ifosfamide solution is, for example, dissolved in a total of 3 liters of 5% dextrose-common salt solution.

There are numerous problems associated with the preparation and processing of ifosfamide. During the preparation of sterile, crystallized ifosfamide a product is obtained having an unstable physical nature. In particular, the fluctuating flow properties greatly impair accuracy of dosage during filling.

The processing of ifosfamide is further impeded by its hygroscopic nature and the low melting point. If stored for a longer period of time the sterile crystallizate sinters and the speed of dissolution falls. As ifosfamide begins to sinter, the clarity and pH value of the solution also decrease with simultaneous yellow discoloration and therapeutic use is then generally no longer possible.

Mesna is also a substance that is only stable and storable under special conditions.

It has not been possible, hitherto, to combine ifosfamide and mesna, even though this would represent a great advantage with regard to storage and practical handling.

SUMMARY OF THE INVENTION

The object of the invention is therefore to make available ifosfamide and mesna in a form which has improved properties such as improved pharmaceutical quality, dosability and solubility, which is easier to use and, in particular, which is suitable for the preparation of injectable solutions.

It has now surprisingly been found that the disadvantages and difficulties in the handling and storage of ifosfamide and mesna, which have been encountered previously, can be overcome by the use of a particular ifosfamide-mesna lyophilizate.

Accordingly, the present invention provides a lyophilized preparation consisting of ifosfamide, 0.05–1.0 parts by weight of mesna and 0.1 to 17 parts by weight of a hexitol, the amount of mesna and hexitol being, in each case, based on one part by weight of ifosfamide as well as optionally other conventional pharmaceutical auxiliary substances. Preferably, the hexitol is mannitol.

The present invention also provides a process for the preparation of an ifosfamide-mesna lyophilizate in which an aqueous or aqueous-ethanolic solution of ifosfamide and mesna, as well as a hexitol and optionally other pharmaceutical auxiliary substances, is frozen under an inert gas at between −70° C. and 0° C. and the water is removed from the product so-obtained in the frozen state. Preferably, the non-adsorptively bound water is removed at a temperature between −30° C. and +40° C. and a pressure between $10^3$ to 10 mbar and subsequently adsorptively bound water is removed at a temperature between 0° C. and 40° C. and a pressure between $10^4$ and $10^1$.

It is particularly surprising that, in the lyophilizate of the invention, the ifosfamide has a better heat stability than the dry filled ifosfamide used in the past.

After a storage time of only 1 month at 40° C., dry filled ifosfamide turns dark; after 2 months, the contents of the bottle sinter and show a yellow discoloration. At a storage temperature of 55° C. dry filled ifosfamide has already melted after 4 days. In contrast, the lyophilizate of the present invention displays neither discoloration nor change in the consistency of the ifosfamide when stored under the conditions mentioned above. Nor are there any changes in the mesna.

The speed of dissolution of the ifosfamide-mesna lyophilizate of the present invention is markedly higher compared to the dry filled ifosfamide. Whereas the lyophilizate dissolves immediately on addition of the solvent, regardless of the duration of storage, injection bottles containing the previously-known dry filling have to be thoroughly shaken for ½ to 3 minutes after the solvent is injected into them. Should complete dissolution not occur immediately—and this applies in the case of injection bottles stored for a longer period of time—it is even necessary to allow the solution to stand for a few minutes. This renders clinical use of the preparation more difficult.

Unlike the sterile crystallizate, the ifosfamide-mesna lyophilizate of the present invention will continue to display optimum solubility properties, even after storage for several years. In addition, dry filled ifosfamide (that is pure ifosfamide crystallizate) is much more sensitive to humidity than the lyophilizate of the present invention. Thus, dry filled ifosfamide liquefies even at a relative humidity of less than 75%, whereas, even at 100% relative humidity, the lyophilizate of the present invention, although becoming moist, retains its initial shape.

Moreover, the risk of particulate or microbial contamination when filling the sterile crystallizate is considerably greater than in the case of the lyophilizate of the present invention.

In contrast, when preparing the ifosfamide-mesna lyophilizate of the present invention, the sterile filtration of the solution is only carried out immediately before filling into injection bottles. There is, therefore, greater microbiological safety than when filling the sterile crystallizate used previously. In addition, particulate impurities, which occasionally give rise to complaints following dry filling, can be avoided more reliably by filtering the solution.

Moreover, the lyophilization of ifosfamide in combination with mesna not only leads to an improvement in the product, but its preparation and practical use are also more economical than the separate preparation of sterile crystallizate and mesna injection solution.

Moreover, the combination of the invention also has a surprisingly improved action on administration as compared to the previously separate administration of ifosfamide and mesna. Thus, for example, the combination of the invention, when given as an intravenous, continuous infusion (for example with a composition containing 5.0 g of ifosfamide + 2.0 g of mesna) provides continuous uroprotection due to the simultaneous continuous renal elimination of urotoxic metabolites and mesna. This minimizes reduction in the uroprotecting effect resulting from emptying of the bladder. The fixed dosage relationship of ifosfamide and mesna in the lyophilizate when used as a continuous intravenous infusion (for example 5 g of ifosfamide +2 g of mesna for 6 hour, or 10 g of ifosfamide +4 g of mesna for 24 hour continuous infusion) prevents the insufficient uroprotection which can occur with repeated bolus injection of mesna or also insufficient infusion dosage. The use of the combination lyophilizate as a short-term infusion for 30 minutes to 2 hours in the amounts of, for example, 500 mg to 5 g of ifosfamide together with 20% of the ifosfamide amount in the form of mesna guarantees adequate uroprotection in the first 4 hours. Preferred dosages for use in humans are, for example:

0.5 g of ifosfamide+0.1 g of mesna
1 g of ifosfamide+0.2 g of mesna
2 g of ifosfamide+0.4 g of mesna
5 g of ifosfamide+1.0 g of mesna
5 g of ifosfamide+2.0 g of mesna It has been found that only the process of the invention which uses a hexitol, such as for example mannitol, produces an improved ifosfamide-mesna lyophilizate. It was, for example, not possible to obtain a lyophilizate through the admixture of common salt, as is for example conventional for the dry filling of other oxazaphosphorins.

In accordance with the invention, for example, an aqueous solution containing 1-13 percent by weight of ifosfamide and 0.05-13 parts by weight of mesna as well as 0.1-17 parts by weight of hexitol as cross-linking agent, based on one part by weight of ifosfamide, is freeze dried. This aqueous solution preferably contains 5-12 percent by weight of ifosfamide and 0.5-12 percent by weight of mesna, in particular 8-10 percent by weight of ifosfamide and 0.8-10 percent of mesna.

It is also possible to use corresponding ethanol-water solutions of ifosfamide and mesna in place of a purely aqueous solution (ethanol proportion of such a solution up to 45% m/m[1], for example 1-20% of ethanol). In such cases the ethanol is, if possible, first removed in a vacuum before the remaining ice is sublimed. The conditions for the preliminary removal of ethanol are, for example: pressure 5–10[1] mbar, temperature from −25° C. rising to −5° C. over 10 hours, the temperature of the regulating plates then being raised to 15° C. In any given case, these conditions also depend on the thicknesses of the layer of the material to be dried in the injection bottles and must be varied accordingly.

[1] Definition according to the Deutsches Arzneibuch 9th Ed.: percent mass/mass

The amount of hexitol in the aqueous or aqueousethanolic solution is generally 1-17, preferably 3-12, in particular 5-9 percent by weight. If the amount of hexitol is based on one part by weight of ifosfamide, then the amount of hexitol is 0.1-17, preferably 1 to 2.5, in particular 0.6-0.8 parts by weight of hexitol per 1 part by weight of ifosfamide. Based on 1 part by weight of mesna, the amount of hexitol is, for example, 0.1-17, preferably 1-6, in particular 3 –4 parts by weight.

Hexitols that may be used are: mannitol, glucitol (sorbitol such as D-sorbitol), dulcitol, allitol, altritol (e.g. D- and L-altritol), iditol (e.g. D- and L-iditol), their optically active forms (D- or L-forms) as well as the corresponding racemates. In particular mannitol is used, such as D-mannitol, L-mannitol, DL-mannitol, and of these preferably D-mannitol. The hexitol used may also be mixtures of the above mentioned hexitols, e.g. mixtures of mannitol and sorbitol and/or dulcitol.

In addition to the hexitol, it is also possible to add other conventional pharmaceutical auxiliary substances such as, for example, glycine, lactose, polyvinylpyrrolidone, glucose, fructose, albumin and equivalent cross-linking substances. The total amount of such substances in the solution used for the freeze drying is, for example, 0-16.8 parts by weight based on 1 part by weight of ifosfamide or mesna. In the final lyophilizate the total amount of such auxiliary substances may be up to 16.8 parts by weight, based on one part by weight of hexitol. In any given case, the amount of such auxiliary substances depends on the amount of hexitol present, to such an extent that the total amount of hexitol and that of other auxiliary substances in the finished lyophilizate shall not exceed 17 parts by weight, based on 1 part of ifosfamide or mesna. For example, should the lyophilizate only contain 0.1 parts by weight of hexitol, up to 16.9 parts by weight of other auxiliary substances may be present; if for example 8.5 parts by weight of hexitol are present, the amount of other auxiliary substances may, for example, be up to 8.5 parts by weight, based on 1 part of ifosfamide or mesna.

For the preparation of the solution to be used for freeze drying about 70 to 80%, preferably 75% of the required amount of water or water and ethanol are prepared and the corresponding amounts of ifosfamide, mesna and mannitol are dissolved one after the other (that is the ifosfamide is added first, then the mesna and subsequently the hexitol [e.g. mannitol]) stirring continuously, for example with continuous agitation. An inactive gas such as, for example, nitrogen, carbon dioxide or an inert gas (e.g. helium) is passed through the water used for the preparation of the solution to displace the oxygen. The inactive gas is also passed through the solution during preparation of the solution. The removal of oxygen is important, since mesna is easily oxidized to the disulfide. After dissolution is complete the final volume is made up and the pH is measured. The pH of this solution should, for example, be between 4 and 7 after dilution. For purposes of pH measurement a 4% solution, based on the ifosfamide, is preferably prepared.

The ifosfamide-mesna solution thereby obtained is then sterilized by filtration through conventional, pathogen-proof filters, nitrogen being used as the pressure gas. If operating at room temperature (18° C. to 22° C.), the storage time until filling into the injection vessels should not exceed a time of 3–4 hours, including the time used to prepare the solution.

Should the subsequent freeze drying not be possible immediately, a solution of this type, optionally also after filling into the injection vessels, may still be stored for example for up to 36 hours at low temperatures for example between 5° and +10° C., preferably +4° to +6° C., before freeze drying.

To carry out the process of the invention the ifosfamide-mesna solution so obtained is filled into containers for injection preparations, for example ampoules or other glass vessels. The containers are flushed before and after filling with sterile and particle-free inert gas (e.g. nitrogen). The freeze drying stoppers are then inserted and freeze drying commenced.

For sterilization, conventional pathogen-proof filters, for example conventional bacteria filters with a pore size of about 0.2 $\mu$m, are used. The glass vessels or ampoules used are sterilized beforehand in a conventional manner.

The hexitol used (preferably mannitol, in particular D-mannitol) should conform to the requirements of the British Pharmacopoeia 1980.

The hexitol used must be pyrogen-free (pyrogens are fever-inducing endotoxins which are formed by bacteria). The same applies to the ifosfamide and mesna used. The removal or destruction of pyrogens is effected in a conventional manner (for example the solution of active substance is treated with active charcoal before sterile filtration). In addition the injection water used must be sterile and pyrogen-free and conform to the requirements of the Deutsches Arzneibuch, 9th edition, 1986.

The injection vessels should appropriately be of tubular glass or blow-molded glass of the IIIrd hydrolytic class (for example 10 R, 30 R and 50 H). (See in this connection Deutsches Arzneibuch, 9th edition, 1986, pages 161–164 and DIN standards 58366, part 1 and part 5). In addition the injection vessels as well as the remaining auxiliary substances, such as rubber stoppers and flanged caps, must fulfill the requirements of DIN standards 58366, part 2 and part 3 as well as 58367, part 1.

The amounts of ifosfamide-mesna solutions which are to be lyophilized in the corresponding containers (ampoules) or other containers for injection preparations are, for example, between 1 and 500, preferably 1 and 250, in particular 2 and 50 ml. In each case the containers are of such a size that the lyophilizate contained therein can subsequently be dissolved in a larger amount of liquid. They should therefore in general be of a volume that is sufficient to prepare a ready-to-use final solution that contains about 2 to 5, preferably 2 to 4, in particular 2 to 2.5 times the volume of the lyophilizate solution originally filled therein.

As already mentioned, each ampoule or glass vessel is preferably filled with a single dose of ifosfamide and mesna, the amount of ifosfamide per glass vessel being for example between 100 mg and 10 g, preferably 200 mg to 5 g, and the amount of mesna being 10 mg to 10 g, preferably 20 mg to 5 g. The solution is subsequently freeze dried in this glass vessel or ampoule in a conventional manner. It is, however, also possible to lyophilize larger amounts of ifosfamide-mesna, that is a correspondingly larger solution volume of the ifosfamide-mesna solution in a correspondingly larger vessel and subsequently to divide or fill the lyophilizate obtained into correspondingly smaller dosages.

The lyophilization itself is conducted in such a way that the ampoules or glass vessels or other vessels which contain the ifosfamide-mesna solution are inserted directly on a regulating plate or in trays on a regulating plate in a freeze drying chamber. After closing the chamber, the ampoules or vessels are cooled to temperatures below 0° C. so that the water freezes out completely. For example cooling is effected down to temperatures between $-70°$ C. to 0° C., preferably between $-70°$ C. and $-5°$ C., in particular $-50°$ C. to $-30°$ C., or $-45°$ C. to $-35°$ C. As soon as the solutions are completely frozen, the freeze drying chamber is gradually evacuated and the drying process begins. This involves first removing the non-adsorptively bound solvent at temperatures between $-30°$ C. to $+40°$ C., preferably 0° C. to $+30°$ C., in particular $+10°$ C. to $+20°$ C., a pressure between $10^3$ to 6, preferably $10^2$ to 2, in particular $10^1$ to 1 mbar being set. The above mentioned temperatures or temperature ranges are the temperatures of the regulating plates. In so doing, the process is controlled so that the heat applied above the plate temperature is used up completely as heat of sublimation and the temperature of the frozen ifosfamide-mesna- containing solution always remains below its eutectic temperature. The desired temperature of the regulating plate can, in each case, be programmed for example by programming discs or by computer. The duration for the removal of this non-adsorptively bound solvent depends on the size of the individual containers and is for example between about 8 to 50 hours at a plate temperature of $+15°$ C. and a pressure of 0.8 mbar. For example reference is made in this connection to the times mentioned in the example.

The complete removal of the non-adsorptively bound water can be demonstrated as follows: non-adsorptively bound water is present in the form of ice. The so-called pressure increase measurement is used to ascertain whether such water is still present in the lyophilizate. For this purpose, a valve situated between the drying chamber and condenser room, to which the vacuum pump is also connected, is closed. Any ice present would then quickly sublimate and lead to a pressure increase in the drying chamber. In the pressure increase measurement, the pressure in the chamber may rise from the starting value, for example 0.8 mbar, to a maximum of 1 mbar after 15 minutes. Any greater increase would indicate that the main drying was not yet completed.

Residual adsorptively bound solvent is then removed by means of post-drying. This takes for example 3 to 12 hours under a vacuum of $10^1$ to $10^4$ mbar, in particular 3–4 hours under a vacuum of $10^{-3}$ to $10^{-4}$ mbar.

The lyophilization process is completed when the residual moisture (determined by the method of K. Fischer) lies below 1%, preferably below 0.5%. In particular, post-drying to remove adsorptively bound water occurs at temperatures between 0 and 40, preferably 10 to 35, in particular 20° to 30° C. and a pressure between $10^4$ to $10^1$, preferably $10^3$ to $10^2$, in particular $10^3$ to $5 \times 10^3$ mbar, this post-drying taking for example 2 to 36, preferably 6 to 24, in particular 3 to 12 hours.

When the freeze drying is complete the vessels are closed. All stages of the process of the invention are carried out under aseptic conditions.

The injection bottles are then closed, for example after ventilating the freeze drying chamber to normal pressure through the addition of a dry inert gas (e.g. nitrogen) with special freeze drying rubber stoppers which are silicon-treated to prevent abrasion and in order to improve their sliding properties.

With the exception of the freezing and the removal of the solvent in a vacuum, all operations are undertaken in a non-reactive gas atmosphere (e.g. nitrogen, carbon dioxide, inert gases such as helium).

DETAILED DESCRIPTION OF PREFERRED EMBODIMENTS

The following examples illustrate the invention.

Example 1

The following solution is used for freeze drying:

| | |
|---|---|
| Mesna | 20 mg |
| Ifosfamide | 100 mg |
| D-mannitol | 70 mg |
| Water for injection purposes ad | 1 ml |

The density of this solution is 1.061 g/ml at +20° C.

The amount of solution to be prepared depends on the filling and freeze drying capacity available.

All steps in the process of preparing and filling the solution are carried out under nitrogen or with nitrogen being passed through the solution. Preparation of the solution:

Ca. 80% of the amount of water for injection purposes is prepared and the corresponding amounts of mesna, ifosfamide and mannitol are dissolved in the water, one after another, with continuous stirring and the passage of nitrogen. After complete dissolution, the final volume is made up and the pH measured.

The finished solution is sterilized using the pathogen-proof filters conventionally used for this purpose (for example Sartorius SM 11107 or SM 11307, 0.2 μμm pore size, Pall Filter NRP (pore size 0.2 μm), and stored until filling while avoiding particulate and bacterial contamination. The pressure gas used for filtration purposes is nitrogen. Storage at room temperature (20–22° C.) should not exceed 3–4 hours, including the time required to prepare the solution. If freeze drying does not take place immediately, the solution may be stored for about 36 hours at +4° C. to +6° C.

For purposes of sterile filtration, it is also possible to use additional conventional pre-filters (for example Sartorius SM 13400 or Pall LPA) to protect the sterile filter.

Cleaning the Injection Bottles

The injection bottles are rinsed with demineralized hot and cold water and with air. All cleaning media are freed of suspended matter by means of filtration.

The bottles are dried using hot air and sterilized (discontinuously at 180° C./2 hours) while avoiding recontamination with particles from the air.

The rubber stoppers used to close the injection bottles are cleaned using demineralized water and, for example, a cleaning agent consisting of non-ionogenic surfactants and phosphoric acid esters in aqueous solution.

The cleaned stoppers are rinsed free of fibers and threads using demineralized water or filtered demineralized water. The stoppers cleaned in this manner are then sterilized using steam.

The injection bottles, cleaned and sterilized in this manner, are then filled aseptically with the ifosfamide-mesna solution and closed with rubber stoppers, the vessels being flushed out with nitrogen before and after filling. Filling amounts:

| Ifosfamide | Mesna | Filling amount | Volume administered* |
|---|---|---|---|
| 200 mg | 40 mg | 2 ml | 5 ml |
| 500 mg | 100 mg | 5 ml | 12.5 ml |
| 1 g | 0.2 g | 10 ml | 25 ml |
| 2 g | 0.4 g | 20 ml | 50 ml |
| 5 g | 1.0 g | 50 ml | 125 ml |
| 5 g | 2.0 g | 50 ml | 125 ml |

*for the subsequent dilution of the lyophilizate

The filling volumes should not exceed the following limits:

| Filling volume | Limiting value of single filling vol. | Average limiting value of filling volume |
|---|---|---|
| 2 ml | 1.9–2.1 ml | 1.95–2.05 ml |
| 5 ml | 4.8–5.2 ml | 4.9–5,1 ml |
| 10 ml | 9.7–10.3 ml | 9.85–10.15 ml |
| 20 ml | 19.4–20.6 ml | 19.7–20.3 ml |
| 50 ml | 48.5–51.5 ml | 49.25–50.75 ml |

The filling volumes should be monitored statistically, the filling volume per filling point being measured at least once every 30 minutes.

The filled injection bottles are frozen to −40° C. as quickly as possible.

The conditions for the freeze drying depend on the sizes of the injection bottles. The following values apply for example:

Duration of main drying at a plate temperature of +15° C. and 0.6 mbar:
ca. 8–10 hours for vessels with
  200 mg of ifosfamide +40 mg of mesna
ca. 12–15 hours for vessels with
  500 mg of ifosfamide +100 mg of mesna
ca. 13–16 hours for vessels with
  1000 mg of ifosfamide +200 mg of mesna
ca. 25–32 hours for vessels with
  2000 mg of ifosfamide +400 mg of mesna
ca. 44–50 hours for vessels with
  5000 mg of ifosfamide +1000 mg of mesna
Duration of post-drying ca. 3–4 hours under a vacuum of $5 \times 10^4$ mbar, at a plate temperature of +25° C.

The residual moisture (determined after K. Fischer) should be less than 0.5%.

The injection bottles are closed at the end of the freeze drying process.

To secure the rubber stoppers, flanged caps are placed in position and rolled on. The finished injection bottles are checked for mechanical defects (cracks, faulty closure, etc.).

Example 2

The following solution is used for freeze drying:

| | |
|---|---|
| Mesna | 100 mg |
| Ifosfamide | 100 mg |
| D-mannitol | 70 mg |
| Water for injection purposes ad | 1 ml |

The density of this solution is 1.101g/ml at +20° C. The amount of solution to be prepared depends on the filling and freeze drying capacity available.

All steps in the process of preparing and filling the solution are carried out under nitrogen or with the passage of nitrogen.

Preparation of the Solution

Ca. 80% of the amount of water for injection purposes is prepared and the corresponding amounts of mesna, ifosfamide and mannitol are dissolved in the water one after another with continuous stirring and with nitrogen being passed through. After complete dissolution, the final volume is made up and the pH measured.

The final solution is sterilized using pathogen-proof filters as conventionally used for this purpose (for example pore size 0.2 μm), and stored until filling while avoiding particulate and bacterial contamination. The gas used for filtration under pressure is nitrogen. Storage time at room temperature (20-22° C.) should not exceed 3-4 hours, including the time required to prepare the solution. If freeze drying does not take place immediately, the solution may be stored for about 36 hours at +4° C. to +6° C.

For purposes of sterile filtration it is also possible to use additional conventional pre-filters (for example Sartorius SM 13400 or Pall LPA) to protect the sterile filter.

Cleaning the Injection Bottles

The injection bottles are rinsed with demineralized hot and cold water and with air. All cleaning media are freed of suspended matter by means of filtration.

The bottles are dried using hot air and sterilized (discontinuously at 180° C./2 hours) while avoiding recontamination with particles from the air.

The rubber stoppers used to close the injection bottles are cleaned using demineralized water and, for example, a cleaning agent consisting of non-ionogenic surfactants and phosphoric acid esters in aqueous solution.

The cleaned stoppers are rinsed free of fibers and threads using demineralized water or filtered demineralized water. The stoppers cleaned in this manner are then sterilized using steam.

The injection bottles cleaned and sterilized in this manner are now filled aseptically with the ifosfamide-mesna solution and closed with rubber stoppers, the vessels being flushed out with nitrogen before and after filling. Filling amounts:

| Ifosfamide | Mesna | Filling amount | Volume administered* |
|---|---|---|---|
| 200 mg | 200 mg | 2 ml | 5 ml |
| 500 mg | 500 mg | 5 ml | 12.5 ml |
| 1 g | 1 g | 10 ml | 25 ml |
| 2 g | 2 g | 20 ml | 50 ml |
| 5 g | 5 g | 50 ml | 125 ml |

*for the subsequent dilution of the lyophilizate

The filling volumes should not exceed the following limits:

| Filling volume | Limiting value of single filling vol. | Average limiting value of filling volume |
|---|---|---|
| 2 ml | 1.9-2.1 ml | 1.95-2.05 ml |
| 5 ml | 4.8-5.2 ml | 4.9-5,1 ml |
| 10 ml | 9.7-10.3 ml | 9.85-10.15 ml |
| 20 ml | 19.4-20.6 ml | 19.7-20.3 ml |
| 50 ml | 48.5-51.5 ml | 49.25-50.75 ml |

The filling volumes should be monitored statistically, the filling volume per filling point being measured at least once every 30 minutes.

The filled injection bottles are frozen to −40° C. as quickly as possible.

The conditions for freeze drying depend on the sizes of the injection bottles. The following values apply for example:

Duration of main drying at a plate temperature of +15° C. and 0.6 mbar:

ca. 8-10 hours for vessels with
200 mg of ifosfamide +200 mg of mesna ca. 12-15 hours for vessels with
500 mg of ifosfamide +500 mg of mesna ca 13-16 hours for vessels with
1 g of ifosfamide +1 g of mesna ca. 25 -32 hours for vessels with
2 g of ifosfamide +2 g of mesna ca. 44-50 hours for vessels with
5 g of ifosfamide +5 g of mesna Duration of post-drying ca. 3-4 hours under a vacuum of $5 \times 10^4$ mbar, at a plate temperature of +25° C. The residual moisture (determined by the method of K. Fischer) should be less than 0.5%. The injection bottles are closed at the end of the freeze drying process. To secure the rubber stoppers, flanged caps are placed in position and rolled on. The finished injection bottles are checked for mechanical defects (cracks, faulty closure, etc.).

What is claimed is:

1. A lyophilized preparation consisting of ifosfamide, 0.05-1.0 parts by weight of sodium-2-mercaptoethane sulfonate and 0.1 to 17 parts by weight of a hexitol, the mesna and hexitol being in each case based on one part by weight of ifosfamide, as well as 0 to 16.9 parts by weight, based on 1 part by weight of ifosfamide, or pharmaceutical auxiliary substances.

2. A lyophilized preparation according to claim 1 in which the hexitol is mannitol.

3. A lyophilized preparation as set forth in claim 1 in which the total amount of hexitol and pharmaceutical auxiliary substances is at most 17 parts for each part of ifosfamide.

4. A process for the preparation of an ifosfamide-sodium-2-marcaptoethane sulfonate lyophilizate which comprises freezing an aqueous or aqueousethanolic solution containing 1 to 13 percent by weight of ifosfamide as well as 0.05-13 parts by weight of sodium-2-mercaptoethane sulfonate 0.1 to 17 parts by weight of hexitol, the amounts of sodium-2-mercaptoethane sulfonate and hexitol in each case being based on one part by weight of ifosfamide, and 0 to 16.9 parts by weight, based on 1 by weight of ifosfamide, of pharmaceutical auxiliary substances under an inert gas at between $-70°$ C. and $0°$ C. and removing the water from the product so-obtained, in the frozen state.

5. A process according to claim 4 in which the hexitol is mannitol.

6. A process according to claim 4 in which nonadsorptively bound water is first removed at a temperature between $-30°$ C. and $+40°$ C. and a pressure between $10^3$ to 10 mbar and subsequently adsorptively bound water is removed at a temperature between $0°$ C. and $40°$ C. and a pressure between $10^4$ and $10^1$.

7. A process according to claim 6 in which the hexitol is mannitol.

8. An ifosfamide-sodium-2-mercaptoethane sulfonate lyophilizate obtained by the process of any claim 4.

* * * * *